United States Patent
Hofmann

(10) Patent No.: US 10,803,587 B2
(45) Date of Patent: Oct. 13, 2020

(54) METHOD FOR PERFORMING AN IMAGING EXAMINATION

(71) Applicant: Siemens Healthcare GmbH, Erlangen (DE)

(72) Inventor: Christian Hofmann, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 107 days.

(21) Appl. No.: 16/018,216

(22) Filed: Jun. 26, 2018

(65) Prior Publication Data
US 2019/0005647 A1    Jan. 3, 2019

(30) Foreign Application Priority Data
Jun. 29, 2017 (EP) .................... 17178749

(51) Int. Cl.
| | |
|---|---|
| *G06T 7/00* | (2017.01) |
| *A61B 6/03* | (2006.01) |
| *A61B 6/00* | (2006.01) |
| *G06T 7/11* | (2017.01) |
| *A61B 5/08* | (2006.01) |

(Continued)

(52) U.S. Cl.
CPC .......... *G06T 7/0016* (2013.01); *A61B 5/0803* (2013.01); *A61B 6/032* (2013.01); *A61B 6/541* (2013.01); *A61B 6/545* (2013.01); *G06T 7/11* (2017.01); *G06T 7/20* (2013.01); *G06T 11/005* (2013.01); *A61B 6/5205* (2013.01); *G06T 2207/10081* (2013.01)

(58) Field of Classification Search
CPC .................................... A61B 6/03; A61B 6/06
See application file for complete search history.

(56) References Cited

U.S. PATENT DOCUMENTS

| | | | |
|---|---|---|---|
| 4,994,965 A | 2/1991 | Crawford et al. | |
| 2005/0201509 A1* | 9/2005 | Mostafavi ............ | A61B 5/1135 378/8 |

(Continued)

FOREIGN PATENT DOCUMENTS

EP    0370341 A2    5/1990

OTHER PUBLICATIONS

European search report for EP17178749 dated Dec. 20, 2017.

*Primary Examiner* — Wen W Huang
(74) *Attorney, Agent, or Firm* — Harness, Dickey & Pierce, P.L.C.

(57) ABSTRACT

A method is disclosed for performing an imaging examination of a patient via a computer tomograph. The method includes: capturing a respiratory movement of the patient; determining a respiration-correlated parameter, from the respiratory movement of the patient; specifying a measurement region of the imaging examination the measurement region including at least one z-position; automatically calculating at least one measurement parameter in accordance with the respiratory movement, using the respiration-correlated parameter as an input parameter; and performing the imaging examination of the patient, in accordance with the at least one measurement parameter in the measurement region via the computer tomograph, to capture the projection data, wherein the projection data, when captured, depicts the respiratory cycle of the patient at the at least one z-position over the complete time duration of the respiratory cycle.

22 Claims, 3 Drawing Sheets

(51) Int. Cl.
G06T 7/20 (2017.01)
G06T 11/00 (2006.01)

(56) References Cited

U.S. PATENT DOCUMENTS

| | | | |
|---|---|---|---|
| 2007/0116171 A1* | 5/2007 | Hsieh | A61B 6/4085 |
| | | | 378/8 |
| 2011/0286574 A1* | 11/2011 | Suzuki | A61B 6/032 |
| | | | 378/8 |
| 2012/0014499 A1 | 1/2012 | Feuerlein | |
| 2013/0041271 A1* | 2/2013 | Ben-Ari | A61B 5/024 |
| | | | 600/506 |
| 2014/0355736 A1* | 12/2014 | Harada | A61B 6/03 |
| | | | 378/16 |

* cited by examiner

FIG 4

| ApM[1/min] | T$_{cycle}$[s] | T$_{rot}$[s] | ΔT$_{rel}$[%] | I$_{ges}$[mAs] | I$_{tube}$[mA] | I$_{rot}$[mAs] | theta[°] | BQ |
|---|---|---|---|---|---|---|---|---|
| 6 | 10.0 | 0.35 | 5 | 500 | 50 | 17.50 | 514.29 | 9000 |
| 9 | 6.7 | 0.35 | 5 | 500 | 75 | 26.25 | 342.86 | 9000 |
| 12 | 5.0 | 0.35 | 5 | 500 | 100 | 35.00 | 257.14 | 9000 |
| 18 | 3.3 | 0.35 | 5 | 500 | 150 | 52.50 | 171.43 | 9000 |

METHOD FOR PERFORMING AN IMAGING EXAMINATION

PRIORITY STATEMENT

The present application hereby claims priority under 35 U.S.C. § 119 to European patent application number EP17178749.2 filed Jun. 29, 2017, the entire contents of which are hereby incorporated herein by reference.

FIELD

At least one embodiment of the invention generally relates to a method for performing an imaging examination of a patient via a computer tomograph, the associated computer tomograph and an associated computer program product.

BACKGROUND

Three-dimensional 3D images of a measurement region extending in a z-direction are normally used for irradiation planning for a patient with a pulmonary or abdominal carcinoma, for example. Using a computer tomograph, in particular projection data from which the 3D images can be reconstructed can be captured during an imaging examination. The imaging examination via the computer tomograph usually requires ionizing x-rays. The 3D images comprise in particular a plurality of slice images of the patient.

In order that an anatomy of the patient, in particular the pulmonary or abdominal carcinoma, which is relevant for the irradiation planning can be reconstructed in a specific respiratory phase of the patient, a respiratory movement of the patient is captured in real time during the imaging examination. The slice images over all respiratory phases of a respiratory cycle, which represents in particular an inhalation and exhalation of the patient and corresponds to a periodic segment of the respiratory movement, are preferably reconstructed for each z-position of the measurement region. This results in the generation of 4D images or respiration-correlated series of 3D images. It is thereby possible in particular to ensure that the dose distribution is adapted in a particularly suitable manner to a planned target volume which is moving.

SUMMARY

The inventor has discovered that an image quality of the 4D images is critical to the irradiation planning. Of primary relevance to the image quality are measurement parameters of the imaging examination, the measurement parameters being preferably so calculated as to be optimal.

The inventor has further discovered that until now, the measurement parameters have typically been chosen from a list containing measurement parameters for the imaging examination which are unchangeable, particularly by a user. The unchangeable measurement parameters are not usually optimized in relation to the image quality. The inventor has further discovered that this has the disadvantage that an operating error by the user will cause an unsuitable set of measurement parameters to be chosen.

At least one embodiment of the invention specifies a method which is individually tailored to the patient for the purpose of performing an imaging examination of a patient via a computer tomograph, the associated computer tomograph and an associated computer program product.

Advantageous developments are specified in the claims.

At least one embodiment of the invention is described below with reference to both a computer tomograph and a method. Features, advantages or alternative embodiment variants cited here can be transferred likewise to the other claimed subject matter and vice versa. In other words, those representational claims directed at the computer tomograph, for example, are also developed by the features described or claimed in connection with the method. The corresponding functional features of the method take the form of corresponding representational modules in this case.

At least one embodiment of the inventive method for performing an imaging examination of a patient via a computer tomograph comprises:

capturing a respiratory movement of the patient, wherein a respiration-correlated parameter $T_{cycle}$ which describes a time duration of a respiratory cycle of the respiratory movement is determined from the respiratory movement of the patient, specifying a measurement region of the imaging examination, wherein the measurement region has at least one z-position, automatically calculating at least one measurement parameter in accordance with the respiratory movement, wherein the respiration-correlated parameter $T_{cycle}$ is used as an input parameter for the automatic calculation of the at least one measurement parameter, such that when the imaging examination is performed in accordance with the at least one measurement parameter, projection data at the at least one z-position can be captured over the complete time duration of the respiratory cycle, and performing the imaging examination of the patient in accordance with the at least one measurement parameter in the measurement region via the computer tomograph, wherein the projection data is acquired which depicts the respiratory cycle of the patient at the at least one z-position over the complete time duration of the respiratory cycle.

The computer tomograph according to at least one embodiment of the invention comprises a planning unit, an arithmetic unit, and a measuring unit having at least one x-ray source and at least one x-ray detector, the computer tomograph being designed to execute a method according to at least one embodiment of the invention.

At least one embodiment of the invention is directed to a computer program product which can be loaded directly into a memory of the programmable arithmetic unit has program code segments/modules for executing a method according to at least one embodiment of the invention when the computer program product is executed in the arithmetic unit.

At least one embodiment of the invention is directed to a non-transitory computer-readable medium including program code segments which, when executed by a computer, cause the computer program segments to execute a method according to at least one embodiment of the invention.

BRIEF DESCRIPTION OF THE DRAWINGS

The invention is described and explained in greater detail below with reference to the example embodiments illustrated in the figures, in which:

FIG. 4 shows a table of example measurement parameters which are calculated in accordance with an example embodiment of the inventive method.

DETAILED DESCRIPTION OF THE EXAMPLE EMBODIMENTS

Figure 1:
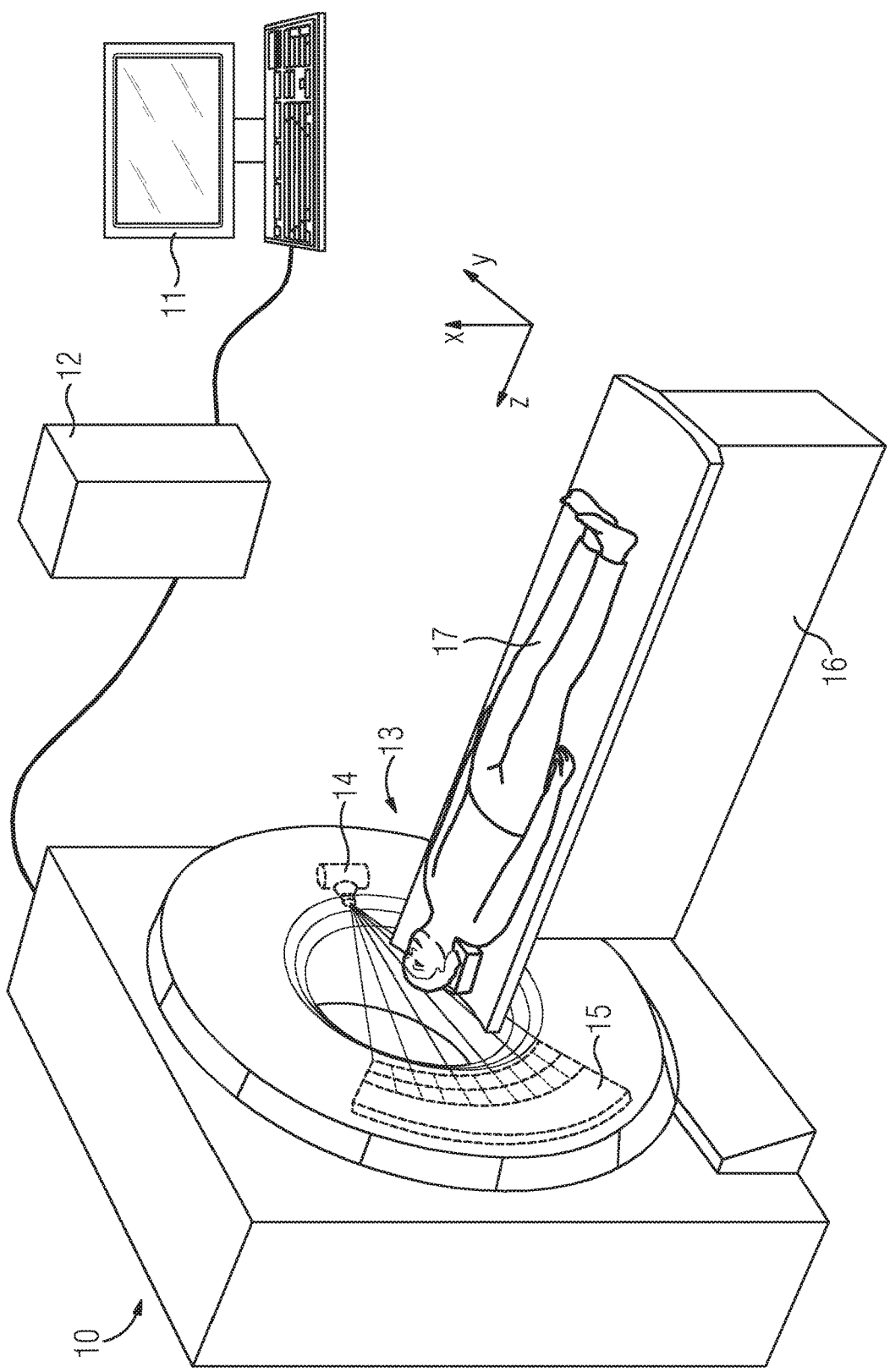
FIG. 1 shows a computer tomograph according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive method for performing an imaging examination of a patient via a computer tomograph comprises:

capturing a respiratory movement of the patient, wherein a respiration-correlated parameter $T_{cycle}$ which describes a time duration of a respiratory cycle of the respiratory movement is determined from the respiratory movement of the patient, specifying a measurement region of the imaging examination, wherein the measurement region has at least one z-position, automatically calculating at least one measurement parameter in accordance with the respiratory movement, wherein the respiration-correlated parameter $T_{cycle}$ is used as an input parameter for the automatic calculation of the at least one measurement parameter, such that when the imaging examination is performed in accordance with the at least one measurement parameter, projection data at the at least one z-position can be captured over the complete time duration of the respiratory cycle, and performing the imaging examination of the patient in accordance with the at least one measurement parameter in the measurement region via the computer tomograph, wherein the projection data is acquired which depicts the respiratory cycle of the patient at the at least one z-position over the complete time duration of the respiratory cycle.

The capture of the respiratory movement of the patient is effected in particular via a sensor, e.g. via a camera or a respiratory belt. The respiratory movement usually describes an unrestricted respiration of the patient and comprises in particular at least one respiratory cycle of the patient. The respiratory movement is captured in particular over the complete respiratory cycle of the patient, wherein the complete respiratory cycle comprises at least one single inhalation and one single exhalation of the patient. The respiratory cycle preferably corresponds to a periodic segment of the respiratory movement. The time duration of the periodic segment corresponds to the time duration of the respiratory cycle.

The determination of the respiration-correlated parameter $T_{cycle}$ is effected in particular automatically in accordance with a suitable algorithm. The slower the respiration of the patient, the higher in particular the respiration-correlated parameter $T_{cycle}$. The respiration-correlated parameter preferably corresponds to the time duration of the respiratory cycle.

The specification of the measurement region of the imaging examination can be effected by a user of the computer tomograph. For this purpose, the computer tomograph has a planning unit, which has a monitor and at least one input device. The user specifies the measurement region in particular via the at least one input device on a graphical user interface of the monitor. For example, overview images which are reconstructed from overview data captured during an overview measurement are displayed to the user on the graphical user interface. The measurement region of the imaging examination could in principle be specified automatically, in particular via sensor-based scanning of the patient and/or via landmark recognition.

The measurement region of the imaging examination extends in particular along a longitudinal axis running in a longitudinal direction of the patient. The longitudinal axis of the patient is preferably parallel to a longitudinal axis which runs in a longitudinal direction of a patient couch. A z-direction of the computer tomograph normally corresponds to the longitudinal axis of the patient couch. The measurement region comprises the at least one z-position, wherein the at least one z-position describes a position of a slice along the longitudinal axis of the patient couch. The slice along the longitudinal axis of the patient couch is depicted by a slice image in particular.

The slice image has in particular a slice thickness extending in a z-direction of the computer tomograph. The measurement region preferably comprises a 3D volume extending in a z-direction of the computer tomograph. In this case, it is possible to reconstruct either a single slice image with a large slice thickness or a plurality of slice images with a small slice thickness. It is usual for correspondingly more slice images to be reconstructed as the slice thickness of the respective slice images decreases.

At least three parameter groups can be distinguished in the context of the imaging examination. The first parameter group comprises in particular fixed parameters which are predetermined by the patient or by a technical embodiment of the computer tomograph, for example. Examples of fixed parameters include an age of the patient or a tube detector speed, which describes the speed at which at least one x-ray source of the computer tomograph and at least one x-ray detector of the computer tomograph can rotate around the patient. In particular, the respiration-correlated parameter $T_{cycle}$ is assigned to the first parameter group.

The second parameter group comprises modifiable parameters which can be specified in particular by the user of the computer tomograph, e.g. via the graphical user interface. Examples of modifiable parameters include a total dose $I_{ges}$, which is directly proportional to a further measurement variable of a radiation dose CTDI (Computed Tomography Dose Index) of the patient during the imaging examination, and a reconstruction kernel for reconstruction of a slice image from the projection data. The total dose $I_{ges}$ determines in particular the image quality of the slice image and the radiation dose of the patient during the performance of the imaging examination.

The third parameter group comprises dependent parameters which can be calculated from e.g. parameters of the first parameter group and/or the second parameter group. For example, a reconstruction angular interval theta can be calculated. The at least one measurement parameter can usually be assigned to the third parameter group. The automatic calculation of the at least one measurement parameter in accordance with the respiratory movement describes in particular the automatic calculation of a dependent parameter from the third parameter group in accordance with a fixed parameter from the first parameter group, in particular in accordance with the respiration-correlated parameter $T_{cycle}$.

The respiration-correlated parameter $T_{cycle}$ and a modifiable parameter from the second parameter group are taken as the input parameters for the automatic calculation, in particular in such a way that the projection data at the at least one z-position can be acquired over the complete time duration of the respiratory cycle when the imaging examination is performed. In other words, the at least one measurement parameter is automatically calculated in such a way that the projection data at the at least one z-position is captured for each time point of the respiratory cycle.

It is therefore possible by way of the projection data at the at least one z-position to depict the inhalation and the exhalation of the patient at the at least one z-position during the imaging examination. If the projection data at the at least one z-position depicts the respiratory cycle of the patient over the complete time duration of the respiratory cycle, this is usually referred to as a respiration-correlated imaging examination.

The automatic calculation comprises in particular at least one formula, wherein the at least one measurement parameter is automatically calculated in accordance with the at least one formula in such a way that, when the imaging examination is performed, the projection data at the at least one z-position can depict the respiratory cycle of the patient over the complete time duration of the respiratory cycle. The respiration-correlated parameter $T_{cycle}$ then represents in particular an arithmetic element in the formula by which the at least one measurement parameter is automatically calculated.

The automatic calculation is effected in particular in an arithmetic unit of the computer tomograph. For this purpose, the arithmetic unit advantageously has a memory into which program code segments/modules can be loaded. The program code segments/modules comprise in particular the at least one formula for automatic calculation of the at least one measurement parameter.

The automatic calculation is particularly advantageous because the at least one measurement parameter is automatically calculated for each patient individually and therefore the imaging examination is adapted to the patient in a particularly suitable manner because the at least one measurement parameter is not selected from predetermined parameter sets which are averaged over a patient group.

If the imaging examination is performed using a pitch, the patient couch is moved continuously through a maximum field of view of the computer tomograph. This procedure is normally referred to as spiral acquisition of projection data. Typical values of a pitch when performing a measurement in the computer tomograph are above 0 and below 2. As an alternative to the spiral acquisition, the patient couch can be moved in discrete steps through the maximum field of view of the computer tomograph. In this case, after each discrete step, the projection data for the at least one z-position is preferably captured over the complete time duration of the respiratory cycle.

The pitch is proportional to a table advance of the patient couch and an extent of the x-ray detector in a z-direction of the computer tomograph. The maximum field of view depends in particular on the extent. The imaging examination is preferably performed with a small pitch in the order of 0.1 and a minimum tube rotation time Trot of the computer tomograph of 0.5 s.

The pitch corresponds in particular to a ratio between the minimum tube rotation time $T_{rot}$ and the respiration-correlated parameter $T_{cycle}$. The minimum tube rotation time $T_{rot}$ is usually set specifically for each computer tomograph by the technical embodiment and cannot be changed. The lower the minimum tube rotation time $T_{rot}$, the higher the tube detector speed, and the faster the x-ray source and the x-ray detector in particular rotate around the patient and/or the more projection data is captured per time unit. The at least one x-ray source and the at least one x-ray detector in particular usually rotate continuously during the imaging examination.

When the patient couch is moved through the maximum field of view, during the acquisition of the projection data, an angle at which the at least one x-ray source and the at least one x-ray detector are situated relative to the patient couch and a current z-position of the patient couch are usually stored, e.g. with reference to the projection data.

The performance of the imaging examination is effected in particular after the at least one measurement parameter has been calculated automatically and preferably in a patient-specific manner, in particular in accordance with the respiratory movement of the patient. According to the proposed procedure, the imaging examination can be advantageously performed in particular because the projection data can depict the respiratory cycle of the patient over the complete time duration of the respiratory cycle. It is thereby possible in particular to suppress artifacts caused by the respiratory movement of the patient.

It is moreover possible by way of the automatic calculation to optimize the imaging examination to the effect that the patient is exposed to the ionizing x-rays in the computer tomograph for no longer than is necessary to capture the projection data at the at least one z-position over the complete time duration of the respiratory cycle.

In particular, no user interaction is required for the automatic calculation of the at least one measurement parameter. An erroneous specification of the at least one measurement parameter can be avoided thereby.

The projection data depicts the respiratory cycle of the patient over the complete time duration of the respiratory cycle at the at least one z-position. Image data, in particular the slice image, is typically reconstructed from the acquired projection data and stored in a database and/or displayed on the monitor for evaluation by a doctor. The reconstructed slice image is advantageously used as a basis for producing a radiation therapy plan.

According to an embodiment variant, the respiration-correlated parameter $T_{cycle}$ is determined by dividing the respiratory movement into periodic segments and calculating the time duration of the respiratory cycle in accordance with a median of time durations of the periodic segments. The division of the respiratory movement preferably generates a sample of periodic segments, wherein the time duration is calculated for each periodic segment in particular and the median of the time durations is then derived. The respiration-correlated parameter $T_{cycle}$ can be determined in particular on the basis of the time durations calculated thus. The median of the time durations, in particular the time durations calculated thus, is typically set as respiration-correlated parameter $T_{cycle}$.

According to an embodiment variant, the respiration-correlated parameter $T_{cycle}$ is adapted according to a standard deviation of the time durations of the periodic segments. The standard deviation of the time durations of the periodic segments can be calculated from the sample of the periodic segments. The standard deviation provides in particular a measure for any irregularity of the time durations of the periodic segments and therefore the measure for the irregularity of the respiratory movement of the patient. The respiration-correlated parameter $T_{cycle}$ is multiplied by a factor, the factor in particular being higher the greater the standard deviation. The factor is in particular always higher than one in this case.

According to an embodiment variant, the automatic calculation of the at least one measurement parameter comprises calculating a tube current $I_{tube}$ of the computer tomograph during the imaging examination in such a way that the tube current $I_{tube}$ is indirectly proportional to the respiration-correlated parameter $T_{cycle}$. The higher the respiration-correlated parameter $T_{cycle}$, the lower in particular the tube current $I_{tube}$. It follows that the tube current $I_{tube}$ is preferably lower, the slower the patient breathes. If the tube current $I_{tube}$ is indirectly proportional to the respiration-correlated parameter $T_{cycle}$, the total dose $I_{ges}$ in particular is held constant. As a result of automatically calculating the at least one measurement parameter in this way, the total dose $I_{ges}$ of the imaging examination is advantageously not changed.

According to an embodiment variant, the automatic calculation of the at least one measurement parameter comprises calculating a slice-effective tube current-time product $I_{rot}$ in such a way that the slice-effective tube current-time product $I_{rot}$ corresponds to a product of the tube current $I_{tube}$ of the computer tomograph during the imaging examination and the minimum tube rotation time $T_{rot}$ of the computer tomograph during the imaging examination. The higher the tube current $I_{tube}$, the higher in particular the slice-effective tube current-time product $I_{rot}$. Equally, the slice-effective tube current-time product $I_{rot}$ is higher, the higher the minimum tube rotation time $T_{rot}$ of the computer tomograph during the imaging examination. The slice-effective tube current-time product $I_{rot}$ provides in particular a measure of an emitted x-ray quantity and is typically proportional to the radiation dose. The higher the slice-effective tube current-time product $I_{rot}$, the higher generally the radiation dose.

The tube current $I_{tube}$, which is indirectly proportional to the respiration-correlated parameter $T_{cycle}$, is used in particular for the calculation of the slice-effective tube current-time product $I_{rot}$.

The reconstruction angular interval theta specifies in particular an angular interval for the reconstruction of the slice image. The reconstruction angular interval theta comprises in particular an angular range of at least 180°, which usually represents a minimum for the reconstruction of the slice image. The greater the reconstruction angular interval theta, the more projection data with the at least one angle within the reconstruction angular interval theta is used during the reconstruction of the slice image. If the reconstruction angular interval theta is at least 180°, it is usually possible to minimize those image artifacts in the slice image which are caused in particular by a reconstruction angular interval smaller than 180°.

According to an embodiment variant, the automatic calculation of the at least one measurement parameter comprises calculating a reconstruction angular interval theta for the at least one z-position in such a way that the reconstruction angular interval theta for the at least one z-position is directly proportional to the respiration-correlated parameter $T_{cycle}$. The reconstruction angular interval theta is in particular greater, the higher the respiration-correlated parameter $T_{cycle}$ or the slower the patient breathes. The reconstruction angular interval theta depends in particular on the respiration-correlated parameter $T_{cycle}$, and therefore the reconstruction angular interval theta is automatically calculated in a patient-specific manner in such a way that in particular the projection data at the at least one z-position depicts the respiratory cycle of the patient over the complete time duration of the respiratory cycle.

According to an embodiment variant, the automatic calculation of the at least one measurement parameter comprises calculating the reconstruction angular interval theta for the at least one z-position in such a way that the reconstruction angular interval theta for the at least one z-position is indirectly proportional to the minimum tube rotation time $T_{rot}$ of the computer tomograph during the imaging examination. The reconstruction angular interval theta is in particular smaller, the greater the minimum tube rotation time $T_{rot}$ of the computer tomograph during the imaging examination. The reconstruction angular interval theta is in particular smaller, the lower the tube detector speed. The reconstruction angular interval theta depends in particular on the minimum tube rotation time $T_{rot}$ of the computer tomograph during the imaging examination, and therefore the reconstruction angular interval theta is automatically calculated in accordance with the technical embodiment of the computer tomograph in such a way that in particular the projection data at the at least one z-position depicts the respiratory cycle of the patient over the complete time duration of the respiratory cycle.

According to an embodiment variant, the automatic calculation of the at least one measurement parameter comprises holding constant a product of the reconstruction angular interval theta for the at least one z-position and the slice-effective tube current-time product $I_{rot}$ of the computer tomograph during the imaging examination. For example, if the reconstruction angular interval theta is multiplied by a factor, the slice-effective tube current-time product $I_{rot}$ of the computer tomograph during the imaging examination is automatically multiplied by a reciprocal fraction of this factor. In particular, the image quality BQ of the slice image is thereby held constant for the whole of the patient. If slice images are reconstructed at different z-positions in each case, the slice images preferably exhibit the same image quality BQ.

According to an embodiment variant, the projection data is captured in at least one angle relative to the patient and the projection data with the at least one angle within a reconstruction angular interval theta for the at least one z-position is selected as a basis for reconstructing a slice image at the at least one z-position. The projection data includes in particular the current z-position of the patient couch during the imaging examination and in particular the at least one angle of the at least one x-ray source and the at least one x-ray detector during the imaging examination. The projection data in the at least one angle within the reconstruction angular interval theta is preferably used for the reconstruction of the slice image at the at least one z-position.

If a plurality of slice images are reconstructed, the projection data in the at least one angle of the respective reconstruction angular interval theta is preferably used for the reconstruction of an individual slice image in particular. In other words, the reconstruction angular interval theta covers at least 180° for each reconstructed slice image.

If the projection data at the at least one z-position is captured over the complete time duration of the respiratory cycle, it is particularly advantageous to reconstruct not only the slice image, but temporally resolved slice images from the projection data at the at least one z-position. The respiratory cycle of the patient can usually be more simply and better depicted in the temporally resolved slice images than in the slice image alone. Temporal resolution of the temporally resolved slice images is limited and/or predetermined in particular by the minimum tube rotation time $T_{rot}$ of the computer tomograph during the imaging examination. For the reconstruction of a temporally resolved slice image of the temporally resolved slice images, the reconstruction angular interval theta preferably covers the angular range of at least 180°.

The temporal resolution defines in particular a maximum temporal coherence of structures which are moved by the respiratory movement, in particular a skin surface, an organ, a carcinoma and/or a tumor of the patient. If the temporal resolution N comprises seconds, the projection data at the at least one z-position is preferably captured in accordance with the reconstruction angular interval theta within N seconds. The maximum temporal coherence can depend on other types of movement of the patient. The maximum temporal coherence during the imaging examination can be optimized in particular if no movement is present, in particular no movement of the structures which are moved by the respiratory movement. In other words, the less movement of the patient, the better the maximum temporal coherence.

According to an embodiment variant, the reconstruction angular interval theta for the at least one z-position is directly proportional to a product of a relative temporal resolution $\Delta T_{rel}$ and the respiration-correlated parameter $T_{cycle}$.

The temporal resolution of the temporally resolved slice images is preferably adapted to the respiratory movement of the patient by defining a relative temporal resolution $\Delta T_{rel}$. The relative temporal resolution $\Delta T_{rel}$ is defined in particular as a percentage, preferably 5%, of the respiration-correlated parameter $T_{cycle}$. In this case, 20 temporally resolved slice images depicting the complete time duration of the respiratory cycle are reconstructed from the projection data at the at least one z-position. The relative temporal resolution $\Delta T_{rel}$ can be assigned to the second parameter group because the relative temporal resolution $\Delta T_{rel}$ can usually be modified, in particular by the user.

If the reconstruction angular interval theta from the automatic calculation is less than 180°, the relative temporal resolution $\Delta T_{rel}$ is preferably adapted automatically, in particular increased, such that the reconstruction angular interval theta is at least 180°. The tube current $I_{tube}$ and the minimum tube rotation time $T_{rot}$ usually remain unchanged in this case. In other words, all patients are preferably measured in such a way that the reconstruction angular interval theta is at least 180°.

According to an embodiment variant, the automatic calculation of the at least one measurement parameter takes
  the respiration-correlated parameter $T_{cycle}$,
  the tube current $I_{tube}$ of the computer tomograph during the imaging examination,
  the slice-effective tube current-time product $I_{rot}$ of the computer tomograph during the imaging examination,
  the minimum tube rotation time $T_{rot}$ of the computer tomograph during the imaging examination,
  the relative temporal resolution $\Delta T_{rel}$ and
  the reconstruction angular interval theta for the at least one z-position into account. According to this embodiment, the at least one measurement parameter can be calculated and specified in a patient-specific manner, in particular taking into account the respiratory movement of the patient.

According to an embodiment variant, the imaging examination of the patient in the measurement region via the computer tomograph is performed in accordance with
  the respiration-correlated parameter $T_{cycle}$,
  the tube current $I_{tube}$ of the computer tomograph during the imaging examination,
  the slice-effective tube current-time product $I_{rot}$ of the computer tomograph during the imaging examination,
  the minimum tube rotation time $T_{rot}$ of the computer tomograph during the imaging examination,
  the relative temporal resolution $\Delta T_{rel}$ and
  the reconstruction angular interval theta for the at least one z-position. According to this embodiment, in particular the imaging examination of the patient is performed in a patient-specific manner, in particular taking into account the respiratory movement of the patient.

According to an embodiment variant, during the performance of the imaging examination, the respiratory movement of the patient is additionally captured in real time and the reconstruction of the slice image at the at least one z-position from the projection data is effected in accordance with a respiratory phase of the respiratory movement of the patient. In particular if temporally resolved slice images are reconstructed at the at least one z-position, the respiratory phase can be assigned to at least one of the temporally resolved slice images. The at least one of the temporally resolved slice images shows in particular the z-position according to the respiratory phase. For example, the respiratory phase to be displayed can be selected by the user on the monitor, and the planning unit displays in particular the at least one of the temporally resolved slice images.

If the measurement region is a 3D volume extending in a z-direction of the computer tomograph and the measurement region comprises a thorax of the patient, for example, in particular the thorax of the patient can be shown on the monitor in accordance with the selected respiratory phase of the patient. For example, the patient can be shown once with inhalation and once with exhalation according to the selection made by the user.

The performance of the imaging examination of the patient in accordance with the at least one measurement parameter in the measurement region via the computer tomograph can comprise in particular the reconstruction of respiration-correlated 4D images or respiration-correlated 3D image series.

The computer tomograph according to at least one embodiment of the invention comprises
a planning unit,
an arithmetic unit, and
a measuring unit having at least one x-ray source and at least one x-ray detector, the computer tomograph being designed to execute a method according to at least one embodiment of the invention.

At least one embodiment of the invention is directed to a computer program product which can be loaded directly into a memory of the programmable arithmetic unit has program code segments/modules for executing a method according to at least one embodiment of the invention when the computer program product is executed in the arithmetic unit.

At least one embodiment of the invention is directed to a non-transitory computer-readable medium including program code segments which, when executed by a computer, cause the computer program segments to execute a method according to at least one embodiment of the invention.

The computer program product may be a computer program or comprise a computer program. It is therefore possible to execute at least one embodiment of the inventive method in a manner which is fast and robust and can be repeated exactly. The computer program product is configured such that it can execute at least one embodiment of the inventive method steps via the arithmetic unit. The arithmetic unit in this case must meet the respective requirements with regard to e.g. a corresponding main memory, a corresponding graphics card or a corresponding logic unit, such that the respective method steps can be executed efficiently.

The computer program product may be stored on a computer-readable medium or on a network or server, for example, from where it can be loaded into the processor of the arithmetic unit, wherein this can be designed as part of the computer tomograph, for example. Furthermore, control information of the computer program product can be stored on an electronically readable data medium. The control information on the electronically readable data medium can be so embodied as to execute a method according to at least one embodiment of the invention when the data medium is used in the arithmetic unit.

Therefore the computer program product can also be the electronically readable data medium. Examples of electronically readable data media include DVD, magnetic tape, fixed disk or USB stick, on which electronically readable control information is stored, in particular software as described above. If this control information software is read from the data medium and stored in the arithmetic unit and/or planning unit and/or measuring unit of the computer tomograph, all inventive embodiment variants of the previously described method can be performed. Therefore at least one embodiment of the invention can also relate to the cited computer-readable medium and/or the cited electronically readable data medium.

FIG. 1 shows an embodiment of inventive computer tomograph 10 comprising a planning unit 11, an arithmetic unit 12 and a measuring unit 13. The measuring unit 13 comprises at least one x-ray source 14 and at least one x-ray detector 15. The patient 17 is arranged on a patient couch 16.

The planning unit 11 can feature the monitor with a graphical user interface and an input device. It is usually possible for a user to interact with the planning unit 11, in particular via the input device. Computer tomograph projection data and/or a slice image can be displayed to the user on the monitor, for example. The user can preferably select a respiratory phase of the patient on the monitor, and the respective slice image is displayed to the user according to the respiratory phase.

The computer tomograph 10 is connected to the planning unit 11 and the arithmetic unit 12 for the purpose of exchanging data.

The computer tomograph 10 can preferably rotate the at least one x-ray source 14 and the at least one x-ray detector 15, these being arranged at a fixed distance relative to each other, around the patient couch 16, in particular the patient 17. As the imaging examination is performed, the computer tomograph 10 captures the angle at which the at least one x-ray source 14 and the at least one x-ray detector 15 are situated relative to the patient couch 17. The computer tomograph 10 preferably assigns a description of the angle to the projection data which is captured in the angle of the at least one x-ray source 14 and of the at least one x-ray detector 15 relative to the patient couch 16, whereby the angle can be taken into account as part of the reconstruction of the slice image from the projection data.

Figure 2:
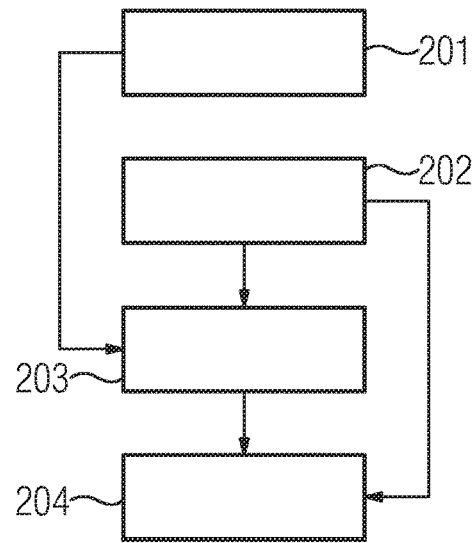
FIG. 2 shows a flow diagram of the method according to an embodiment of the invention.

FIG. 2 shows a flow diagram of an embodiment of the inventive method for performing the imaging examination of the patient 17 via the computer tomograph 10. An embodiment of the inventive method comprises the method steps 201-204.

Method step 201 identifies the capture of a respiratory movement of the patient 17, wherein a respiration-correlated parameter $T_{cycle}$ which describes a time duration of a respiratory cycle of the respiratory movement is determined from the respiratory movement of the patient 17.

Method step 202 identifies the specification of a measurement region of the imaging examination, wherein the measurement region has at least one z-position.

Method step 203 identifies the automatic calculation of at least one measurement parameter in accordance with the respiratory movement, wherein the respiration-correlated parameter $T_{cycle}$ is used as an input parameter for the automatic calculation of the at least one measurement parameter, such that when the imaging examination is performed in accordance with the at least one measurement parameter, projection data at the at least one z-position can be captured over the complete time duration of the respiratory cycle.

The method step 203 has the respiration-correlated parameter $T_{cycle}$ and the at least one z-position as inputs.

Method step 204 identifies the performance of the imaging examination of the patient in accordance with the at least one measurement parameter in the measurement region via the computer tomograph, wherein the projection data is acquired which depicts the respiratory cycle of the patient 17 at the at least one z-position over the complete time duration of the respiratory cycle.

The method step 204 has the measurement region and the at least one automatically calculated measurement parameter as inputs.

Figure 3:
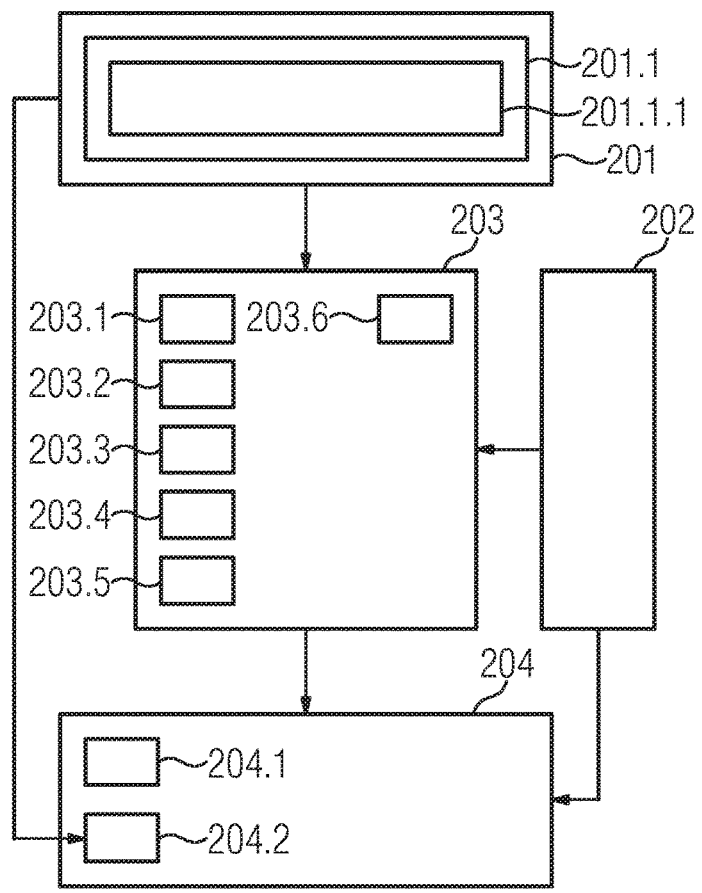
FIG. 3 shows an example embodiment of the method according to an embodiment of the invention.

FIG. 3 shows an example embodiment of the method according to an embodiment of the invention.

The following description is essentially limited to the differences relative to the example embodiment in FIG. 2, reference being made to the description of the example embodiment in FIG. 2 in respect of method steps which remain the same. Those method steps remaining essentially the same are denoted by the same reference numbers in each case.

Method step 201.1 identifies that the respiration-correlated parameter $T_{cycle}$ is determined by dividing the respiratory movement into periodic segments and calculating the time duration of the respiratory cycle in accordance with a median of time durations of the periodic segments.

Method step 201.1.1 identifies that the respiration-correlated parameter $T_{cycle}$ is adapted according to a standard deviation of the time durations of the periodic segments.

Method step 203.1 identifies that the automatic calculation of the at least one measurement parameter comprises calculating a tube current $I_{tube}$ of the computer tomograph 10 during the imaging examination in such a way that the tube current $I_{tube}$ is indirectly proportional to the respiration-correlated parameter $T_{cycle}$.

Method step 203.2 identifies that the automatic calculation of the at least one measurement parameter comprises calculating a slice-effective tube current-time product $I_{rot}$ in such a way that the slice-effective tube current-time product $I_{rot}$ corresponds to a product of the tube current $I_{tube}$ of the computer tomograph during the imaging examination and a minimum tube rotation time $T_{rot}$ of the computer tomograph 10 during the imaging examination.

Method step 203.3 identifies that the automatic calculation of the at least one measurement parameter comprises calculating the reconstruction angular interval theta for the at least one z-position in such a way that the reconstruction angular interval theta for the at least one z-position is directly proportional to the respiration-correlated parameter $T_{cycle}$.

Method step 203.4 identifies that the reconstruction angular interval theta for the at least one z-position is directly proportional to a product of a relative temporal resolution $\Delta T_{rel}$ and the respiration-correlated parameter $T_{cycle}$.

Method step 203.5 identifies that the automatic calculation of the at least one measurement parameter comprises calculating the reconstruction angular interval theta for the at least one z-position in such a way that the reconstruction angular interval theta for the at least one z-position is indirectly proportional to the minimum tube rotation time $T_{rot}$ of the computer tomograph 10 during the imaging examination.

Method step 203.6 identifies that the automatic calculation of the at least one measurement parameter comprises holding constant a product of the reconstruction angular interval theta for the at least one z-position and the slice-effective tube current-time product $I_{rot}$ of the computer tomograph 10 during the imaging examination.

From this procedure, it follows that the automatic calculation of the at least one measurement parameter takes into account the respiration-correlated parameter $T_{cycle}$, the tube current $I_{tube}$ of the computer tomograph 10 during the imaging examination, the slice-effective tube current-time product $I_{rot}$ of the computer tomograph 10 during the imaging examination, the minimum tube rotation time $T_{rot}$ of the computer tomograph 10 during the imaging examination, the relative temporal resolution $\Delta T_{rel}$, and the reconstruction angular interval theta for the at least one z-position.

Method step 204.1 identifies that the projection data is captured in at least one angle relative to the patient 17 and the projection data with the at least one angle within the reconstruction angular interval theta for the at least one z-position is selected as a basis for reconstructing a slice image at the at least one z-position.

From this procedure, it follows that the imaging examination of the patient 17 in the measurement region via the computer tomograph 10 is performed in accordance with the respiration-correlated parameter $T_{cycle}$, the tube current $I_{tube}$ of the computer tomograph 10 during the imaging examination, the slice-effective tube current-time product $I_{rot}$ of the computer tomograph 10 during the imaging examination, the minimum tube rotation time $T_{rot}$ of the computer tomograph 10 during the imaging examination, the relative temporal resolution $\Delta T_{rel}$, and the reconstruction angular interval theta for the at least one z-position.

Method step 204.2 identifies that during the performance of the imaging examination, the respiratory movement of the patient 17 is additionally captured in real time and a reconstruction of the slice image at the at least one z-position from the projection data is effected in accordance with a respiratory phase of the respiratory movement of the patient 17.

The method step 204.2 has the capture of the respiratory movement as per method step 201 as an input.

In the context of this procedure, the method steps 201.1, 201.1.1, 203.1, 203.2, 203.3, 203.4, 203.5, 203.6, 204.1 and 204.2 have been considered jointly. It is obviously also possible for these method steps to be performed individually and/or combined as desired.

A first formula for calculating the dependent parameter $I_{tube}$ is as follows:

$$I_{tube} = \frac{I_{ges}}{T_{cycle}}$$

The tube current $I_{tube}$ has the unit [mA]. The total dose $I_{ges}$ has the unit [mAs]. The respiration-correlated parameter $T_{cycle}$ has the unit [s].

A second formula for calculating the dependent parameter $I_{rot}$ is as follows:

$$I_{rot} = I_{tube} \cdot T_{rot}$$

The slice-effective tube current-time product $I_{rot}$ has the unit [mAs].

A third formula for calculating the dependent parameter theta is as follows:

$$\text{theta} = \frac{\Delta T_{rel} \cdot T_{cycle} \cdot 360°}{T_{rot}}$$

The reconstruction angular interval theta has the unit [°]

A fourth formula for calculating the image quality BQ is as follows:

$$BQ = \text{theta} \cdot I_{rot} = \text{const}$$

The respiration-correlated parameter Tcycle can be converted into a parameter Respiration-Cycles-per-Minute ApM.

FIG. 4 shows a table of example measurement parameters which are calculated in accordance with an embodiment variant of an embodiment of the inventive method, in particular in accordance with the first, second, third and fourth formulas.

The following description is essentially limited to the differences relative to the example embodiment in FIG. 2 and FIG. 3, reference being made to the description of the example embodiment in FIG. 2 and FIG. 3 in respect of method steps which remain the same. Those method steps remaining essentially the same are denoted by the same reference numbers in each case.

The values presented serve merely to illustrate the example embodiment shown here.

FIG. 4 shows that the tube current Itube is indirectly proportional to the respiration-correlated parameter $T_{cycle}$.

FIG. 4 shows that the slice-effective tube current-time product $I_{rot}$ corresponds to a product of the tube current $I_{tube}$ of the computer tomograph 10 during the imaging examination and the minimum tube rotation time $T_{rot}$ of the computer tomograph 10 during the imaging examination.

FIG. 4 shows that the reconstruction angular interval theta for the at least one z-position is directly proportional to a product of the relative temporal resolution $\Delta T_{rel}$ and the respiration-correlated parameter $T_{cycle}$.

FIG. 4 shows that the reconstruction angular interval theta for the at least one z-position is directly proportional to the respiration-correlated parameter $T_{cycle}$.

FIG. 4 shows that a product BQ of the reconstruction angular interval theta for the at least one z-position and the slice-effective tube current-time product $I_{rot}$ of the computer tomograph during the imaging examination is constant.

Although the invention is illustrated and described in detail with reference to the preferred example embodiment, the invention is not restricted by the examples disclosed herein. Variations may be derived therefrom by a person skilled in the art without thereby departing from the scope of the invention as defined by the following patent claims.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for performing an imaging examination of a patient via a computer tomograph, comprising:
    determining a respiration-correlated parameter describing a time duration of a respiratory cycle of a respiratory movement of the patient;
    specifying a measurement region of the imaging examination, the measurement region including at least one z-position;
    calculating at least one measurement parameter based on the respiration-correlated parameter, such that projection data at the at least one z-position is capturable over a complete time duration of the respiratory cycle; and
    capturing the projection data by performing the imaging examination of the patient based on the at least one measurement parameter in the measurement region via the computer tomograph,
    wherein the projection data depicts the respiratory cycle of the patient at the at least one z-position over the complete time duration of the respiratory cycle, and
    the calculating the at least one measurement parameter includes calculating a tube current of the computer tomograph during the imaging examination, the tube current being indirectly proportional to the respiration-correlated parameter, a total dose being constant, the total dose being a product of the tube current and the respiration-correlated parameter.

2. The method of claim 1, wherein the determining the respiration-correlated parameter comprises:
    dividing the respiratory movement into periodic segments; and
    calculating the time duration of the respiratory cycle based on a median of time durations of the periodic segments.

3. The method of claim 2, wherein the determining the respiration-correlated parameter comprises:
    adapting the respiration-correlated parameter according to a standard deviation of the time durations of the periodic segments.

4. The method of claim 2, wherein the calculating the at least one measurement parameter comprises:
    calculating a slice-effective tube current-time product, the slice-effective tube current-time product corresponding to a product of the tube current of the computer tomograph during the imaging examination and a minimum tube rotation time of the computer tomograph during the imaging examination.

5. The method of claim 2, wherein the calculating the at least one measurement parameter comprises:
calculating a reconstruction angular interval for the at least one z-position, the reconstruction angular interval for the at least one z-position being directly proportional to the respiration-correlated parameter.

6. The method of claim 5, wherein the reconstruction angular interval for the at least one z-position is directly proportional to a product of a relative temporal resolution and the respiration-correlated parameter.

7. The method of claim 2, wherein the calculating the at least one measurement parameter comprises:
calculating a reconstruction angular interval for the at least one z-position, the reconstruction angular interval for the at least one z-position being indirectly proportional to a minimum tube rotation time of the computer tomograph during the imaging examination.

8. The method of claim 2, wherein
a product of a reconstruction angular interval for the at least one z-position and a slice-effective tube current-time product of the computer tomograph during the imaging examination are constant.

9. The method of claim 2, wherein the calculating the at least one measurement parameter takes is based on:
a slice-effective tube current-time product of the computer tomograph during the imaging examination;
minimum tube rotation time of the computer tomograph during the imaging examination;
a relative temporal resolution; and
a reconstruction angular interval for the at least one z-position.

10. The method of claim 2, wherein performing the imaging examination of the patient is based on:
a slice-effective tube current-time product of the computer tomograph during the imaging examination;
a minimum tube rotation time of the computer tomograph during the imaging examination;
a relative temporal resolution; and
a reconstruction angular interval for the at least one z-position.

11. The method of claim 1, wherein the calculating the at least one measurement parameter comprises:
calculating a slice-effective tube current-time product, the slice-effective tube current-time product corresponding to a product of the tube current of the computer tomograph during the imaging examination and a minimum tube rotation time of the computer tomograph during the imaging examination.

12. The method of claim 1, wherein the calculating the at least one measurement parameter comprises:
calculating a reconstruction angular interval for the at least one z-position, the reconstruction angular interval for the at least one z-position being directly proportional to the respiration-correlated parameter.

13. The method of claim 12, wherein the reconstruction angular interval theta for the at least one z-position is directly proportional to a product of a relative temporal resolution and the respiration-correlated parameter.

14. The method of claim 1, wherein the calculating the at least one measurement parameter comprises:
calculating a reconstruction angular interval for the at least one z-position, the reconstruction angular interval for the at least one z-position being indirectly proportional to a minimum tube rotation time of the computer tomograph during the imaging examination.

15. The method of claim 1, wherein
a product of a reconstruction angular interval theta for the at least one z-position and a slice-effective tube current-time product of the computer tomograph during the imaging examination are constant.

16. The method of claim 1, wherein the projection data is captured in at least one angle relative to the patient and the projection data, the at least one angle being within a reconstruction angular interval for the at least one z-position, the reconstruction angular interval selected as a basis for reconstructing a slice image at the at least one z-position.

17. The method of claim 1, wherein the calculating the at least one measurement parameter takes is based on:
a slice-effective tube current-time product of the computer tomograph during the imaging examination;
a minimum tube rotation time of the computer tomograph during the imaging examination;
a relative temporal resolution; and
a reconstruction angular interval for the at least one z-position.

18. The method of claim 1, wherein the performing the imaging examination of the patient is based on:
a slice-effective tube current-time product of the computer tomograph during the imaging examination;
a minimum tube rotation time of the computer tomograph during the imaging examination;
a relative temporal resolution; and
a reconstruction angular interval for the at least one z-position.

19. The method of claim 1, wherein the performing the imaging examination comprises:
capturing the respiratory movement of the patient in real time; and
reconstructing a slice image at the at least one z-position from the projection data based on a respiratory phase of the respiratory movement of the patient.

20. A non-transitory computer program product, directly loadable into a memory of a programmable arithmetic unit, including program code segments for executing the method of claim 1 when the computer program product is executed in the arithmetic unit.

21. A non-transitory computer readable medium, storing program code segments for executing the method of claim 1 when the program code segments are executed on a computer.

22. A computer tomograph, comprising:
an x-ray scanner having at least one x-ray source and at least one x-ray detector; and
processing circuitry configured to cause the computer tomograph to,
determine a respiration-correlated parameter describing a time duration of a respiratory cycle of a respiratory movement,
specify a measurement region of an imaging examination, the measurement region including at least one z-position;
calculate at least one measurement parameter, the at least one measurement parameter based on the respiration-correlated parameter, such that projection data at the at least one z-position is capturable over a complete time duration of the respiratory cycle, and
capture the projection data by performing the imaging examination based on the at least one measurement parameter in the measurement region via the computer tomograph, wherein the projection data depicts the respiratory cycle at the at least one z-position over the complete time duration of the respiratory cycle, and the at least one measurement parameter includes a tube current of the computer tomograph during the imaging examination, the tube current being indirectly proportional to the respiration-correlated parameter, a total dose being constant, the total dose being a product of the tube current and the respiration-correlated parameter.

* * * * *